United States Patent
Shellman

(10) Patent No.: US 7,101,385 B2
(45) Date of Patent: Sep. 5, 2006

(54) METHOD FOR ADMINISTERING PHOTOTHERAPY AS A CELLULITE FIRMING TREATMENT

(76) Inventor: Jeremy J. Shellman, 4250 E. Downing St., Mesa, AZ (US) 85205

( * ) Notice: Subject to any disclaimer, the term of this patent is extended or adjusted under 35 U.S.C. 154(b) by 0 days.

(21) Appl. No.: 10/387,204

(22) Filed: Mar. 10, 2003

(65) Prior Publication Data

US 2004/0181210 A1   Sep. 16, 2004

(51) Int. Cl.
    *A61N 5/06*   (2006.01)
(52) U.S. Cl. .................. 607/88; 607/91; 128/898; 606/9
(58) Field of Classification Search ............ 607/88–91; 128/898; 606/9
    See application file for complete search history.

(56) References Cited

U.S. PATENT DOCUMENTS

| | | | | |
|---|---|---|---|---|
| 6,024,760 A * | 2/2000 | Marchesi | ...... | 607/96 |
| 6,402,739 B1 * | 6/2002 | Neev | ...... | 606/9 |
| 6,613,341 B1 * | 9/2003 | Motley et al. | ...... | 424/401 |
| 6,673,096 B1 * | 1/2004 | Lach | ...... | 607/89 |
| 6,960,354 B1 * | 11/2005 | Leigh et al. | ...... | 424/450 |
| 2002/0193831 A1 * | 12/2002 | Smith, III | ...... | 607/2 |
| 2003/0069618 A1 * | 4/2003 | Smith et al. | ...... | 607/100 |

* cited by examiner

*Primary Examiner*—A. Farah

(57) ABSTRACT

A method for firming and removing cellulite comprising: exfoliating an area of a body for treatment of the cellulite; applying an anti-cellulite/firming agent to the area of a body for treatment of the cellulite; and administering light treatment to the area of a body for treatment of the cellulite.

20 Claims, 1 Drawing Sheet

Exfoliate entire area of the body to be treated.

Apply body firm/anti-cellulite substance to the entire area of the body to be treated.

Administer light treatment to the entire area of the body to be treated.

| Exfoliate entire area of the body to be treated. |
|---|

| Apply body firm/anti-cellulite substance to the entire area of the body to be treated. |
|---|

| Administer light treatment to the entire area of the body to be treated. |
|---|

METHOD FOR ADMINISTERING PHOTOTHERAPY AS A CELLULITE FIRMING TREATMENT

BACKGROUND OF THE INVENTION

1. Field of the Invention

This invention relates generally to a cellulite treatment and, more specifically, to a phototherapy treatment which will firm up cellulite in the body.

2. Description of the Prior Art

Cellulite has been a subject of much debate and controversy in the scientific community as well as in the professional skin care and body therapist area. For years, many have argued that cellulite is merely fat and can only be treated with diet and exercise. Every year Americans spend billions of dollars fighting the battle of the bulge. From the latest diets, to supplements, to health club memberships, the weight loss industry is booming and showing no signs of slimming down. However, even non-overweight people who regularly exercise and are active have been known to suffer from cellulite problems. The bottom line is that studies have shown that eighty to ninety percent of women will get cellulite sometime after they reach puberty.

Cellulite may be caused by a number of factors. According to one study, one of the causes of the rippling effect of cellulite is fluid retention in the adipose tissue. The fluid retention not only causes visible swelling, but the toxic waste contained in the fluid breaks down collagen and elastic fibers that help to keep the skin smooth and firm. But, the main cause of cellulite is a decline in the circulatory system. Although toxic accumulation and fluid retention certainly are major contributing factors to cellulite formation, it is poor circulation (blood and lymphatic flow) that ultimately creates the right environment for cellulite formation.

Aside from weight loss, exercise, and liposuction, the number of effective treatments in treating cellulite are limited. Massage therapy was once touted as being effective in treating cellulite. However, deep tissue massages may do more harm than good. By performing a firm kneading type of massage, one may actually stimulate additional fluids into the tissue. Unless one can accompany a deep tissue massage with a means of improving blood and lymph flow out of the tissue, deep tissue massages will only exacerbate cellulite problems. However, lighter forms of massages, known as known as Manual Lymph Drainage, stimulates lymph flow and may be somewhat effective in treating cellulite. This type of massage aids in the elimination of lymph fluids without increasing blood flow. However, this type of massage is difficult to do and requires proper training to perform effectively.

Therefore, a need existed to provide an improved treatment for cellulite. The improved treatment for cellulite must be more effective than those of the prior art.

SUMMARY OF THE INVENTION

In accordance with one embodiment of the present invention, it is an object of the present invention to provide an improved treatment for cellulite.

It is another object of the present invention to provide an improved treatment for cellulite that is more effective than those of the prior art.

BRIEF DESCRIPTION OF THE EMBODIMENTS

In accordance with one embodiment of the present invention, a method for firming and removing cellulite is disclosed. The method comprises: exfoliating an area of a body for treatment of the cellulite; applying an anti-cellulite/firming agent to the area of a body for treatment of the cellulite; and administering light treatment to the area of a body for treatment of the cellulite.

The foregoing and other objects, features, and advantages of the invention will be apparent from the following, more particular, description of the preferred embodiments of the invention, as illustrated in the accompanying drawing.

BRIEF DESCRIPTION OF THE DRAWINGS

The novel features believed characteristic of the invention are set forth in the appended claims. The invention itself, as well as a preferred mode of use, and advantages thereof, will best be understood by reference to the following detailed description of illustrated embodiments when read in conjunction with the accompanying drawings.

DETAILED DESCRIPTION OF THE PREFERRED EMBODIMENT

Figure 1:
FIG. 1 is a simplified flow chart showing the method of the present invention.
Figure 1:

Referring to the FIGURES, a process for administering phototherapy for cellulite/firming treatments is disclosed. The process begins by exfoliating the area to be treated. In general, the entire are to be treated (i.e. both legs, thighs, buttocks, and the like) needs to be exfoliated. Exfoliating may be accomplished in a number of different ways. One way to exfoliate is by dry brushing. Dry brushing is generally done by brushing towards the person's heart. Dry brushing removes dead skin cells and stimulates the skin to eliminate toxins more efficiently. This speeds up the internal cleansing of the body and reduces stress to the kidneys, lungs, and colon, which also assists in the elimination of waste. But more importantly, dry brushing assists in reducing cellulite deposits and tones and tightens the skin. Other benefits of dry brushing include stimulating better blood and lymph circulation and stimulating nerve endings in the skin while also energizing the nervous system Another way to exfoliate the body is to apply an alphahydroxy acid gel/lotion/serum (hereinafter alphahydroxy acid gel) to the area to be treated. In general, alphahydroxy acid gel is applied by hand to the area to be treated. Alphahydroxy acid gel is an exfoliate which helps to remove the outer layer of dead cellular debris, stimulate collagen production, and improve skin texture.

The above are just two ways to exfoliate the body. It should not be seen as to limit the scope of the present invention. One may cleanse the body with an exfoliating body scrub. Others ways may be used to exfoliate the body area without departing from the spirit and scope of the present invention.

Once the body area has been exfoliated, an anti-cellulite/firming lotion is applied to the area. The anti-cellulite/firming lotion may be one of several different items. For example, a body firming serum may be used. The body firming serum is generally applied by hand and firmly massaged into the area until the serum is absorbed into the body. A cellulite cream may also be used. Again, generally speaking, the cellulite cream is generally applied by hand and firmly massaged into the area until the cream is absorbed into the body. One may also use a massage cream or oil. The massage cream/oil is generally applied by hand and lightly massaged into the body. It should be noted that one or more of the above may be used in combination with one another. In general, the body firming and cellulite removing lotions will contain one or more of the following active ingredients: lespedeza capitata, ulva lactuca, glycyrrhiza glabra, combretum, bupleurum extract, caffeine, caffine benzoate, carnitine, palmitoyl carnitine, hydrocotyl extract, licorice extract, niacin, CoA, weet clover, ivy, barley, aminophylline, theophylline, retinoids, kawa-kawa, nutmeg, and capsicum.

After the anti-cellulite/firming lotion is applied, phototherapy is administered. Phototherapy is a light treatment for the skin. Phototherapy can be administered in a number of ways. For example, intense light therapy may be used. Intense light therapy has been shown to provide powerful therapeutic benefits to living tissues and organisms. Both visible red (620 nm to 700 nm) and invisible infrared light (700 nm to 1200 nm) have been shown to effect positive changes at a cellular level. Violet light of 400 nm may also be used. Visible red light, at a wavelength of 660 nm, penetrates human tissue to a depth of about 8–10 mm. Skin layers, because of their high blood and water content, absorb red light very readily. Infrared light at 950 nm, penetrates to a depth of about 30–40 mm which makes it more effective for deep muscle therapy.

Red and infrared light emitting diodes (LED's) and lasers are common sources used for phototherapy. LED's and lasers are similar inasmuch as they can emit the same light but differ in the way the light energy is delivered. Lasers are focused beam single wavelength light emitters that can be intense enough to burn/cut tissue or "cold" enough to only have light therapy effects. LEDs do not deliver enough power to damage the tissue, but they do deliver enough energy to stimulate a response from the body.

In accordance with one embodiment of the present invention, a large LED probe of a photorejuvenation machine is used for the phototherapy. The LED probe is moved by hand over the area to be treated. The LED probe is slowly moved around the entire area to be treated with gentle pressure so little to no light escapes. The LED probe should maintain constant contact with the skin. It should be noted that it is the light itself at a specific wavelength that is therapeutic in nature and not the machine that produces it.

The administration of the light may be done in several different ways. The light should generally be administered in a slow methodical manner to the entire area to be treated. In general, the light should be administered for approximately an hour. If the LED probe is set on a "high setting" (5000 hertz), the light may be administered for approximately 60 minutes. Alternatively, the light may be administered at different levels. For example, the light may be administered for approximately 16–20 on a "low setting" of approximately 20 hertz. Then the light may be administered for an additional 16–20 minutes on a "medium setting" of approximately 150–292 hertz. The light may further be administered for an additional 16–20 minutes on a "high setting" of approximately 5000 hertz.

Light sources which produce pulsed frequencies of 20 hertz, 150 hertz, 292 hertz, and 5000 hertz have been used to reduce cellulite problems. However, it would be beneficial to include all frequencies between 20–5000 hertz as well as a continuous light source rather than a pulsed source.

The light actually stimulates the production of new capillaries which provide for the applied lotions/substances to effectively penetrate the affected area and be distributed throughout the area. The light and the lotions/substances work in conjunction to increase lymphatic vessel diameter and increase lymphatic drainage. This provides for the accumulated toxins and metabolic residues to be expelled from the affected areas. The cells of the affected area receive the light as an energy supplement which in conjunction with the products increases their ability to process the stored lipids for energy. The light and lotions/substances also work in conjunction to promote collagen and elastin synthesis in the affected area thereby providing for firmer skin. Use of the above method has reduced up to 1.75 inches from the waist of one individual after 3 treatments. The above steps should be repeated for proper treatment.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A method for firming and removing cellulite comprising: exfoliating an area of a body for treatment of the cellulite; applying an anti-cellulite/firming agent to the area of a body for treatment of the cellulite; and administering light treatment to the area of a body for treatment of the cellulite.

2. The method of claim 1 wherein exfoliating an area of a body for treatment of the cellulite further comprises dry brushing the area of a body for treatment of the cellulite towards a heart of an individual receiving treatment.

3. The method of claim 1 wherein exfoliating an area of a body for treatment of the cellulite further comprises applying an alphahydroxy acid substance to the area of a body for treatment of the cellulite.

4. The method of claim 1 wherein exfoliating an area of a body for treatment of the cellulite further comprises cleansing the area of a body for treatment of the cellulite with an exfoliating body scrub.

5. The method of claim 1 wherein applying an anti-cellulite/firming agent to the area of a body for treatment of the cellulite further comprises: applying a body firming substance to the area of a body for treatment of the cellulite; and massaging the body firming serum into the area of a body for treatment of the cellulite until absorbed.

6. The method fe of claim 1 wherein applying an anti-cellulite/firming agent to the area of a body for treatment of the cellulite further comprises: applying a cellulite substance to the area of a body for treatment of the cellulite; and massaging the cellulite substance into the area of a body for treatment of the cellulite until absorbed.

7. The method of claim 1 wherein applying an anti-cellulite/firming agent to the area of a body for treatment of the cellulite further comprises: applying a massage cream/oil to the area of a body for treatment of the cellulite; and massaging the massage cream/oil into the area of a body for treatment of the cellulite until absorbed.

8. The method of claim 1 wherein administering light treatment to the area of a body for treatment of the cellulite further comprises administering a light source to the entire area of a body wherein the light source maintains constant contact with the skin so little to no light escapes.

9. The method of claim 8 further comprising administering the light source to the area of a body for treatment of the cellulite for approximately 25–30 minutes when the light source is on a setting of approximately 5000 hertz.

10. The method of claim 8 further comprising: administering the light source to the area of a body for treatment of the cellulite for approximately 8–10 minutes when the light source is on a setting of approximately 20 hertz; administering the light source to the area of a body for treatment of the cellulite for approximately 8–10 minutes when the light source is on a setting of approximately 150–300 hertz; and administering the light source to the area of a body for treatment of the cellulite for approximately 8–10 minutes when the light source is on a setting of approximately 5000 hertz.

11. A method for firming and removing cellulite comprising: exfoliating an area of a body for treatment of the cellulite; applying an anti-cellulite/firming agent to the area of a body for treatment of the cellulite for removing and firming of the cellulite; and administering light treatment to the area of a body for treatment of the cellulite wherein the light treatment will raise body temperature to burn away the cellulite.

12. The method of claim 11 wherein exfoliating an area of a body for treatment of the cellulite further comprises dry brushing the area of a body for treatment of the cellulite towards a heart of an individual receiving treatment.

13. The method of claim 11 wherein exfoliating an area of a body for treatment of the cellulite further comprises applying an alphahydroxy acid substance to the area of a body for treatment of the cellulite.

14. The method of claim 11 wherein exfoliating an area of a body for treatment of the cellulite further comprises cleansing the area of a body for treatment of the cellulite with an exfoliating body scrub.

15. The method of claim 11 wherein applying an anti-cellulite/firming agent to the area of a body for treatment of the cellulite further comprises: applying a body firming substance to the area of a body for treatment of the cellulite; and massaging the body firming serum into the area of a body for treatment of the cellulite until absorbed.

16. The method of claim 11 wherein applying an anti-cellulite/firming agent to the area of a body for treatment of the cellulite further comprises: applying a cellulite substance to the area of a body for treatment of the cellulite; and massaging the cellulite substance into the area of a body for treatment of the cellulite until absorbed.

17. The method of claim 11 wherein applying an anti-cellulite/firming agent to the area of a body for treatment of the cellulite further comprises: applying a massage cream/oil to the area of a body for treatment of the cellulite; and massaging the massage creamfoil into the area of a body for treatment of the cellulite until absorbed.

18. The method of claim 11 wherein administering light treatment to the area of a body for treatment of the cellulite further comprises administering a light source to the entire area of a body wherein the light source maintains constant contact with the skin so little to no light escapes.

19. The method of claim 18 further comprising administering the light source to the area of a body for treatment of the cellulite for approximately 25–30 minutes when the light source is on a setting of approximately 5000 hertz.

20. The method of claim 18 further comprising: administering the light source to the area of a body for treatment of the cellulite for approximately 8–10 minutes when the light source is on a setting of approximately 20 hertz; administering the light source to the area of a body for treatment of the cellulite for approximately 8–10 minutes when the light source is on a setting of approximately 150–300 hertz; and administering the light source to the area of a body for treatment of the cellulite for approximately 8–10 minutes when the light source is on a setting of approximately 5000 hertz.

* * * * *